United States Patent
Padmanabhan et al.

(10) Patent No.: US 9,956,709 B2
(45) Date of Patent: May 1, 2018

(54) HOT MELT FRAGMENTATION EXTRUDER AND PROCESS

(71) Applicant: STEERLIFE INDIA PRIVATE LIMITED, Bangalore (IN)

(72) Inventors: Babu Padmanabhan, Bangalore (IN); Suneela Prodduturi, Hyderabad (IN); Himadri Sen, Pune (IN)

(73) Assignee: SteerLife India Private Limited, Bengaluru, Karnataka (IN)

( * ) Notice: Subject to any disclaimer, the term of this patent is extended or adjusted under 35 U.S.C. 154(b) by 308 days.

(21) Appl. No.: 14/888,916

(22) PCT Filed: May 27, 2014

(86) PCT No.: PCT/IN2014/000358
§ 371 (c)(1),
(2) Date: Nov. 3, 2015

(87) PCT Pub. No.: WO2014/192026
PCT Pub. Date: Dec. 4, 2014

(65) Prior Publication Data
US 2016/0082640 A1  Mar. 24, 2016

(30) Foreign Application Priority Data
May 27, 2013  (IN) .......................... 2295/CHE/2013

(51) Int. Cl.
*B29C 47/00* (2006.01)
*B29C 47/40* (2006.01)
(Continued)

(52) U.S. Cl.
CPC ........ *B29C 47/0011* (2013.01); *A61K 9/1694* (2013.01); *A61K 9/2095* (2013.01);
(Continued)

(58) Field of Classification Search
None
See application file for complete search history.

(56) References Cited

U.S. PATENT DOCUMENTS

| 5,048,971 A | 9/1991 | Wall et al. |
| 5,693,342 A | 12/1997 | Cervos et al. |

(Continued)

FOREIGN PATENT DOCUMENTS

| EP | 1832281 A1 | 9/2007 |
| WO | WO 02/09919 A2 | 2/2002 |

(Continued)

OTHER PUBLICATIONS

Vasanthavada et al., "Application of Melt Granulation Technology Using Twin-screw Extruder in Development of High-dose Modified-release Tablet Formulation," *Journal of Pharmaceutical Sciences*, vol. 100, No. 5, May 2011, pp. 1923-1934, 12 pages.

(Continued)

*Primary Examiner* — Mary Lynn F Theisen
(74) *Attorney, Agent, or Firm* — Klarquist Sparkman, LLP

(57) ABSTRACT

A co-rotating twin screw extruder for forming fragments is disclosed. The extruder comprises of an intake zone for receiving one or more excipient(s) suitable for oral dosage or one or more excipient(s) suitable for oral dosage along with one or more active pharmaceutical ingredient, a melt zone for softening at least one excipient to form a viscous mass or melt and a fragmenting zone for fragmenting and cooling the viscous mass into cooled fragments and an extruder outlet for recovering the cooled fragments from the extruder.

15 Claims, 5 Drawing Sheets

(51) Int. Cl.
  *B29C 47/60*  (2006.01)
  *B29C 47/80*  (2006.01)
  *A61K 9/16*  (2006.01)
  *A61K 9/20*  (2006.01)
  *B29K 91/00*  (2006.01)
  *B29K 105/00*  (2006.01)

(52) U.S. Cl.
  CPC ............ *B29C 47/00* (2013.01); *B29C 47/402* (2013.01); *B29C 47/6075* (2013.01); *B29C 47/805* (2013.01); *B29C 47/807* (2013.01); *A61K 9/1617* (2013.01); *B29K 2091/00* (2013.01); *B29K 2105/0035* (2013.01)

(56) References Cited

U.S. PATENT DOCUMENTS

| | | | |
|---|---|---|---|
| 6,318,650 | B1 | 11/2001 | Breitenbach et al. |
| 6,783,270 | B1* | 8/2004 | Padmanabhan ..... B29C 47/0861 366/82 |
| 2007/0259070 | A1 | 11/2007 | Song et al. |
| 2008/0226731 | A1* | 9/2008 | Vasanthavada ...... A61K 9/2054 424/489 |
| 2011/0063940 | A1 | 3/2011 | Padmanabhan |
| 2011/0092515 | A1* | 4/2011 | Qiu ...................... A61K 9/1652 514/253.06 |
| 2012/0179649 | A1* | 7/2012 | Padmanabhan ..... B29C 47/0844 707/609 |
| 2014/0036614 | A1* | 2/2014 | Padmanabhan ....... B29C 47/627 366/85 |

FOREIGN PATENT DOCUMENTS

| | | |
|---|---|---|
| WO | WO 2013/074951 | 5/2003 |
| WO | WO 2008/132707 A1 | 11/2008 |
| WO | WO 2013/128463 | 9/2013 |

OTHER PUBLICATIONS

International Search Report and Written Opinion from corresponding PCT Patent Application No. PCT/IN2014/000358, dated Jul. 24, 2015, 11 pages.

* cited by examiner

HOT MELT FRAGMENTATION EXTRUDER AND PROCESS

CROSS REFERENCE TO RELATED APPLICATIONS

This is the U.S. National Stage of International Application No. PCT/IN2014/000358, filed May 27, 2014, which was published in English under PCT Article 21(2), which in turn claims the benefit of India Patent Application No. 2295/CHE/2013, filed May 27, 2013. Both applications are hereby incorporated by reference herein.

BACKGROUND

Hot-melt extrusion (HME) is a widely applied technique in the plastics industry and has been demonstrated to be a viable method to prepare several dosage forms of pharmaceutical compositions. Hot-melt extruded dosage forms are typically mixtures of active medicaments, functional excipients, and processing aids. HME also offers several functional advantages over traditional pharmaceutical processing techniques such as wet, dry and melt granulation. Such advantages include absence of solvents, few processing steps, continuous operation, the possibility of the formation of solid dispersions/solid solutions and improved bioavailability. HME process can be carried out in a single screw extruder or a twin-screw extruder. Due to the self-cleaning advantage and configurable mixing capability of the co-rotating twin-screw extruder, the co-rotating twin-screw is increasingly preferred as the device for carrying out the HME process. Conventional HME process involves embedding a drug in a carrier under controlled conditions such as temperature, residence time, mixing energy input, feed rate and pressure and forcing it through an orificed die or an open die to collect the hot viscous mass or melt in the form of a strand, film or a lump. A conventional extruder for HME process includes an intake zone through which the mixture of active ingredients and suitable excipients are introduced, a melt zone for forming a viscous mass or melt and a conveying zone for conveying the hot viscous mass or melt out of the extruder. The barrel in the extruder is divided into different temperature zones that are set to specific temperatures as per the need of the extrusion process. Typically, the temperature of the viscous mass/melt along the length of the barrel is maintained such that there is no solidification inside the extruder. (For example, Vasanthavada et al., 2010 suggest the cooler zone is towards the feeder and the warmer zone towards the exit). Heat for fusion is supplied by the mechanical shear dissipation from the rotating screws inside the extruder as well as from the outside heaters that are typically electrical in nature. The extrudate exiting the extruder is a hot viscous mass or melt that can be shaped to a desired form depending on the shape of the die (cylindrical die yields a strand or slit die yields a film) that can be sized to desired lengths or passed on to a chill roll unit and pressed against the rollers to form thin sheet that will generally flake into smaller pieces.

The extrudate is then subjected to further processing by auxiliary downstream devices, typically a size reduction step to form particles of required size. Free flowing particles are used for compression, capsule filling and/or molding into tablets. Fine particles with narrow size distribution are generally required for oral suspensions. There are limitations on the materials that can be used as carriers; as such materials should be amenable to size reduction since low melting solids cannot be milled effectively and efficiently. The limitation in selection of material that can be size reduced may be a factor in restricting the enhancement in solubility, bioavailability, tastemasking, or sustained release of the pharmaceutical composition.

Spray congealing and spray drying are also known methods for producing fine particles. Spray congealing is carried out by spraying a viscous melt to generate droplets in a cooling chamber. Spray drying is carried out with a fluid material containing solvents that is injected into a heated chamber where the generated droplets are dried to form fine powders. Both processes require large foot-prints for limited capacities of production. Spray congealing is a dedicated facility for limited type of fluid material and offers limited flexibility for varied pharmaceutical preparations. Spray drying involves use of a large amount of solvents that may not meet environmental concerns and does not offer scalability from laboratory equipment to commercial equipment. All batch type processes create variability from lot to lot.

Conventional HME process further requires a multiple equipment setup, under controlled environmental conditions to process pharmaceutical compositions. The process also tends to compromise on one or more desired properties of the pharmaceutical composition.

U.S. Pat. No. 6,318,650 to Breitenbach describes a process for the continuous production of solid, particulate preparations of bioactive substances, in which the bioactive substances are homogeneously dispersed in a matrix of thermoplastic auxiliaries, in a screw extruder having an extruder barrel. The extruder is divided into a plurality of zones, so that the process comprises firstly melting the matrix auxiliaries and mixing the bioactive components with the matrix auxiliaries in a heatable zone of the extruder to form a mixture, and subsequently cooling, precomminuting and finally grinding the mixture in a cooling zone of the extruder to form a powder. It is crucial for success of the process that pure conveying elements are employed in the first part of the cooling zone, in order to minimize the energy input and reduce the shear stress and to maximize the rate of cooling of the melt below the softening point. The process further requires that the matrix polymers are preferably soluble in water but are at least swellable in water. Accordingly, this process is not suitable for all excipients such as fatty acids, glyceryl behenate and waxes; and particularly stearic acid that form a waxy lump on cooling that is not amenable for comminuting inside the extruder. The pure conveying zone resulting in rapid cooling prior to comminuting also produces some powders with exposed active medicament.

It is therefore desirable to have an improved process for the manufacture of pharmaceutical compositions in the form of particles that can enable improved drug delivery systems, using all excipients and particularly excipients such as fatty acids like stearic acid, glyceryl behenate and waxes that are not amenable to milling.

SUMMARY

A co-rotating twin screw extruder for forming fragments is disclosed. The extruder comprises of an intake zone for receiving one or more excipient(s) suitable for oral dosage or one or more excipient(s) suitable for oral dosage along with one or more active pharmaceutical ingredient, a melt zone for softening at least one excipient to form a viscous mass or melt and a fragmenting zone for simultaneous fragmenting and cooling the viscous mass into cooled fragments and an extruder outlet for recovering the cooled fragments from the extruder.

A method of forming fragments within a co-rotating twin screw extruder is disclosed. The method comprises of feeding one or more excipient(s) suitable for oral dosage into the extruder, softening or melting at least one excipient to form a viscous mass or melt, and simultaneously fragmenting and cooling the viscous mass or melt to obtain cooled fragments, and collecting the cooled fragments from the extruder.

DETAILED DESCRIPTION

A co-rotating twin screw extruder for forming fragments is disclosed. The extruder comprises of an intake zone for receiving one or more excipient(s) suitable for oral dosage or one or more excipient(s) suitable for oral dosage along with one or more active pharmaceutical ingredient, a melt zone for softening at least one excipient to form a viscous mass or melt and a fragmenting zone for simultaneous fragmenting and cooling the viscous mass into cooled fragments and an extruder outlet for recovering the cooled fragments from the extruder.

A method of forming fragments within a co-rotating twin screw extruder is disclosed. The method comprises of feeding one or more excipient(s) suitable for oral dosage into the extruder, softening or melting at least one excipient to form a viscous mass or melt, and simultaneously fragmenting and cooling the viscous mass or melt to obtain cooled fragments, and collecting the cooled fragments from the extruder.

Figure 1:
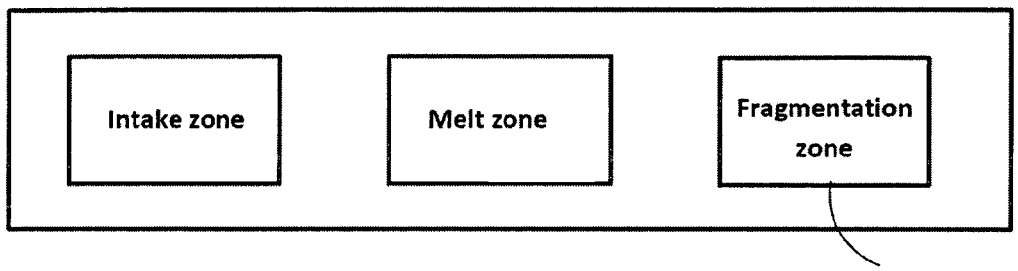
FIG. 1: illustrates the intake zone, the melt zone and the fragmenting zone of the extruder in accordance with an embodiment of the invention.

The present disclosure describes a process for the manufacture of a pharmaceutical composition using an extruder. The pharmaceutical composition comprises of an active pharmaceutical ingredient (API) component and an excipient component. The process involves feeding the active pharmaceutical ingredient (API) component along with the excipient component into an intake zone of the extruder, forming a melt or viscous mass in the melt zone of the extruder and simultaneous fragmenting and cooling the viscous mass or melt in the fragmenting zone of the same extruder. The extrudate obtained is in the form of cooled solid fragments comprising of both the API component and the excipient component. FIG. 1 illustrates the intake zone, the melt zone and the fragmenting zone of the extruder.

The extruder is a fully wiping co-rotating twin-screw extruder. Suitable heating and cooling systems are provided on the extruder barrels to heat or cool the barrels as desired. Any suitable cooling means known to those skilled in the art may be used; for example, a fluid cooling jacket surrounding the barrel, liquid nitrogen, dry ice or the like.

The excipient component includes one or more excipients that serve as a carrier, a filler or a binder for the API component. The excipients could be any pharmaceutical grade material in its solid, semisolid or liquid form. The excipients may be crystalline, amorphous or semicrystalline in nature. Excipients may be hydrophilic, amphiphilic or lipophilic. Excipients may be ionic or non ionic. Excipients may be celluloses such as ethyl cellulose, hydroxypropylcellulose, hydroxypropyl methyl cellulose. Excipient may also be polyethylene glycol, polyethylene oxide, polyvinyl pyrrolidone, copovidone, polyvinyl acetate or poly methacrylates. Excipients may include plasticizers and/or processing aids such as triethyl citrate, triacetin, propylene glycol, dibutyl sebacate, diethyl phthalate, glycerol monostearate. In particular, excipients may also be fatty acids such as stearic acid, glyceryl behenate and waxes. The excipients may also be additives like drug-release modifiers, disintegrants and super disintegrants, thickening agents, bulking agents, binders, flow aids, sweeteners, and anti-oxidants. The choice of excipients may be determined by the person skilled in the art based on properties of the API, desired properties of the pharmaceutical composition and amenable for fragmentation. The formation of the melt or viscous mass involves heating the mixture of the API component and excipient component above the softening or glass transition temperature $T_g$ or the melting point of the excipient(s).

Figure 2:
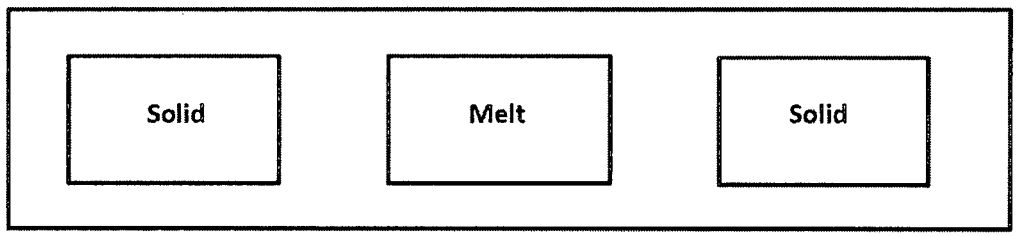
FIG. 2: illustrates a solid input and a cooled solid output from the extruder with an in between continuous semi-solid/viscous phase in accordance with an embodiment of the invention.
Figure 3:
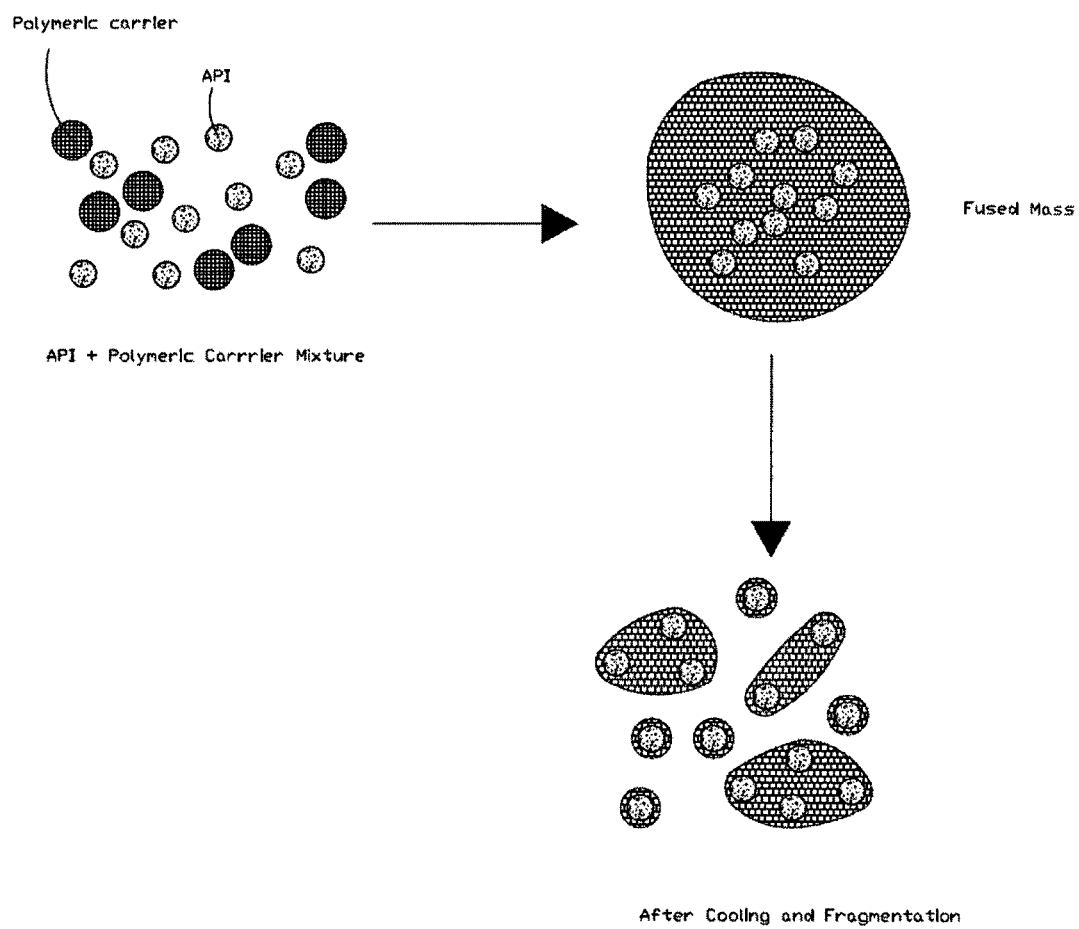
FIG. 3: is a schematic illustration of the disclosed process where a mixture of API(s) and the excipient(s) is fed into the intake zone of the extruder in accordance with an embodiment of the invention.

The temperature and the screw configuration in the melt zone may be such that only the excipient(s) or both the excipient(s) as well as the API soften or melt to form the viscous mass or melt. The excipient(s) or drug(s) used could be either crystalline having sharp melting point or amorphous form with a Tg or softening temperature or semicrystalline with a broad melting point and Tg. Depending on the application and extrusion temperature, the excipient(s) or both excipient(s) and API could be taken into the form of a continuous viscous mass or melt within the extruder followed by fragmentation while cooling within the extruder. The applications include formation of pharmaceutical particles that have one or more of the desired properties not limited to bio-availability enhancement, controlled release, and taste-masking as a result of one or more of the following actions—disrupting the crystal lattice, wetting, encapsulation, complexation, dispersion, formation of solid solution or suspensions, etc. Unlike the conventional hot-melt extrusion where a hot viscous mass is extruded out which is then cooled and particle size reduced post extrusion, in the current hot melt fragmentation process the cooling of the viscous mass or melt is done within the extruder to a temperature at or below the softening temperature or $T_g$ or melting point of the excipient(s) to initiate simultaneous solidification and fragmentation of the viscous mass or melt. This gives cooled solid fragments that are directly obtained from the extruder. The solidified mass is scraped off the extruder surfaces by the extruder elements in the fragmenting zone and fragmented. The cooling and simultaneous fragmentation of the viscous mass or melt at a temperature ranging from Tg or melting point to below the $T_g$ or melting point enables production of increasingly smaller fragments. It is preferred that the cooling be continued to sufficiently below the $T_g$ or melting point of the carrier so as to promote the solidification process, enable further milling and fragmentation and achieve the required particle size distribution. The process as disclosed is therefore a solid input and a cooled solid output from the extruder with an in between continuous semi-solid/viscous phase, as illustrated in FIG. 2. FIG. 3 is a schematic illustration of the disclosed process where a mixture of API(s) and the excipient(s) is fed into the intake zone of the extruder. In the simplest process, a mixture is typically a solid mixture of powders or granules. This mixture is converted into a melt or viscous mass in the melt zone of the extruder. The viscous mass or melt is then fragmented while cooling in the fragmentation zone to obtain cooled solid fragments of well-mixed API component and excipient component.

In accordance with an embodiment, the temperature of the melt in the fragmentation zone should be kept below the softening temperature or $T_g$ or the melting point of the excipient. Lesser cooling in the fragmentation zone results in larger fragments. Greater cooling in the fragmentation zone forms finer fragments. In accordance with an embodiment, a cooling gradient of the melt towards the exit of the extruder may be maintained.

Formation of residue or film on any surface of the extruder in the fragmenting zone may be minimized by the use of suitable extruder elements. The extruder elements used in the fragmenting zone are preferably completely wiping. It is also preferred that such elements have low screw-barrel and screw-screw clearances below 250 microns. In accordance with a preferred embodiment, mixing elements are used in the fragmentation zone. WO 2013/128463 describes a mixing element for distributive mixing having a continuous flight helically formed thereon with a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L'.

The use of at least one mixing element, along with simultaneous cooling permits the process to be applied to all excipients, including fatty acids, glyceryl behenate and waxes; and particularly stearic acid.

In accordance with an embodiment, the mixing elements are used in the beginning of the fragmenting zone, accompanied by simultaneous cooling. The mixing elements are found to be most suitable for initiating the simultaneous cooling and fragmenting step.

Figure 4:
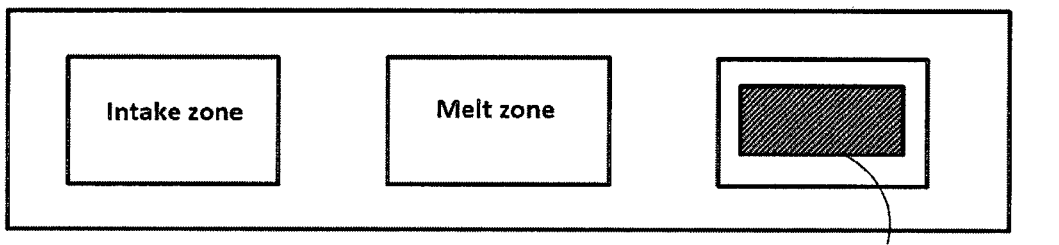
FIG. 4: illustrates the use of milling or fragmenting elements with small clearances generally resulted in finer fragments with significantly reduced or no residue or film development in accordance with an embodiment of the invention.

Use of conventional conveying elements with large clearances in the fragmenting zone was found to form large fragments. In some cases, residue build up was also observed within the extruder. As illustrated in FIG. 4, the use of milling or fragmenting elements with small clearances generally resulted in finer fragments with significantly reduced or no residue or film development. Examples of fragmenting elements include various blocks of two more segments at 30, 45 or 90 degree angles to each other in Forward or Reverse Helix. RKBs are five segment blocks at 45 degree stagger angle. NKBs are five segment blocks at 90 degree stagger angle. The Do/Di (ratio of the outer and inner diameter) of the extruder controls the width of the tip and has an impact on the required particle size distribution as well as preventing residue build up. A large Do/Di can produce finer fragments (as evidenced by experiments).

In accordance with an embodiment, conveying elements are provided towards the end of the fragmenting zone. This assists in conveying the cooled and fragmented particles to the outlet of the extruder.

In accordance with an aspect, the present process allows obtaining pharmaceutical composition having controlled particle size in accordance with the desired application. Depending on the desired drug dosage form, fragments of various size ranges may be obtained. For example—fine fragments for forming oral suspensions, medium to coarse fragments for forming tablets or filling into capsules may be obtained. The present process allows obtaining fragments having discrete particle size distribution i.e. the particle size distribution may be represented by histograms. This has particular advantages during compaction of fragments to form tablet, where smaller fragments can occupy the voids formed between the larger fragments.

The present invention has been illustrated in further detail below by way of examples using Cefuroxime axetil and Ketoprofen as API's with various excipients.

EXAMPLES

A series of trials were conducted using Cefuroxime axetil and Ketoprofen as API with different excipients under varying process conditions such as—screw configuration, barrel temperatures to determine the effect thereof on the particle size distribution of the pharmaceutical composition prepared in accordance with the present invention. Experiments were also conducted using only the excipient component to study the effect of various polymers on the particle size distribution under the varying process conditions.

Figure 5:
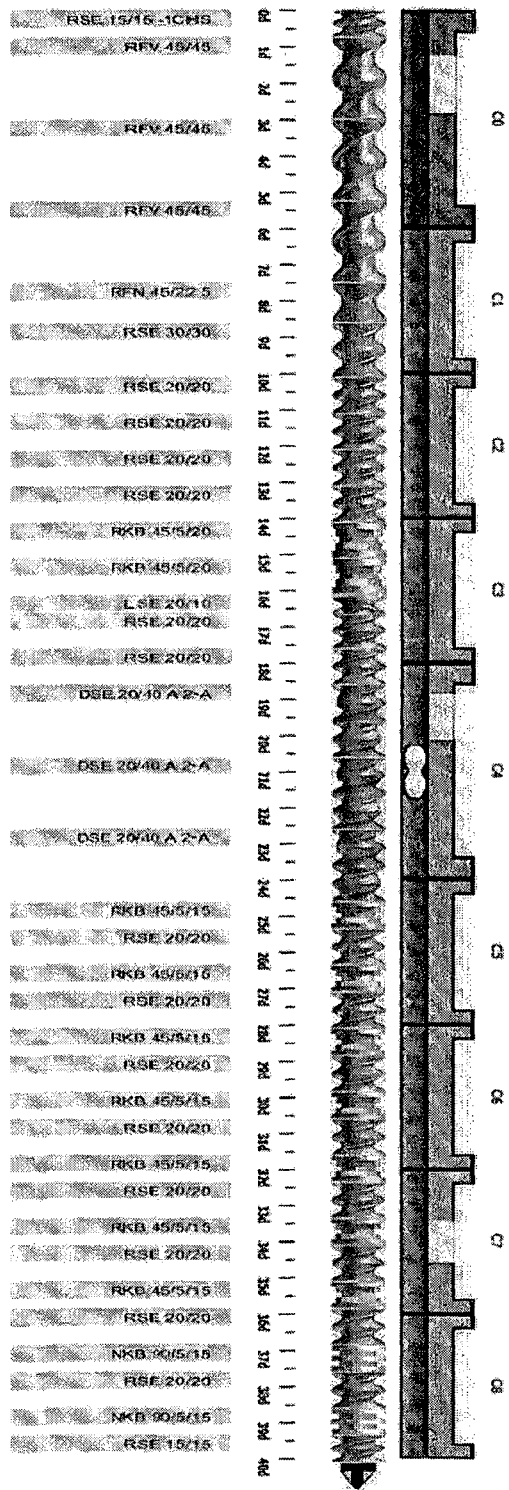
FIG. 5: illustrates a F1 type screw configuration in accordance with an embodiment of the invention.
Figure 6:
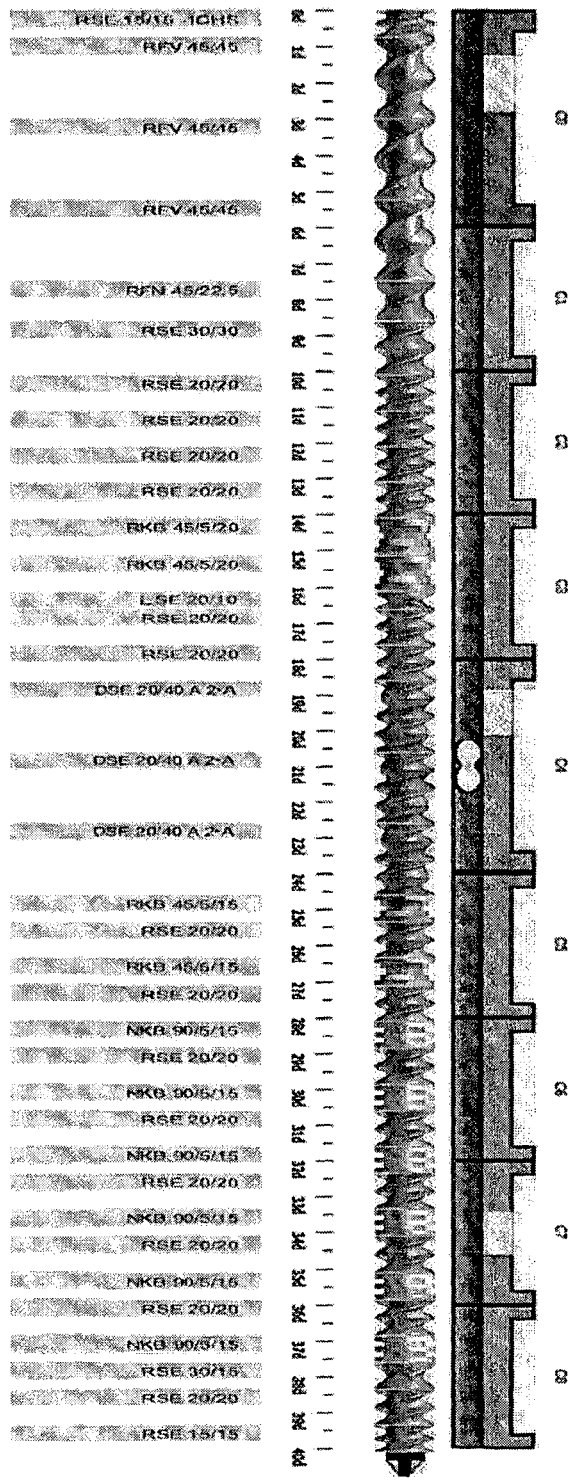
FIG. 6 illustrates a F2 type screw configuration in accordance with an embodiment of the invention.
Figure 7:
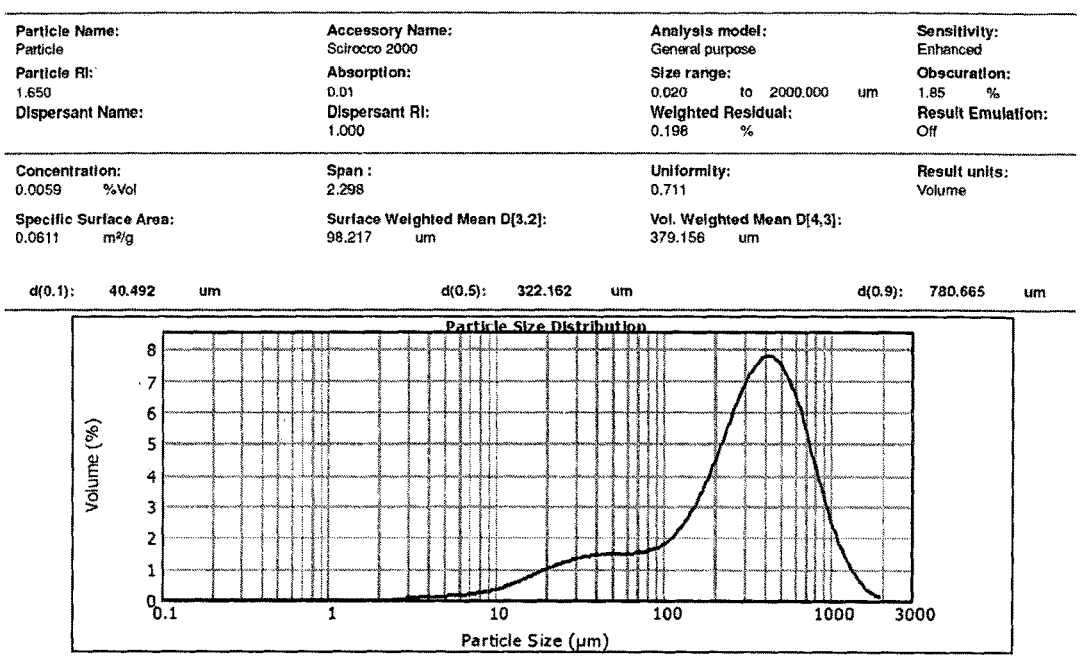
FIG. 7: shows the particle size analysis report for pharmaceutical composition prepared according to trial 12 in accordance with an, embodiment of the invention.

Excipients:

The trials were performed using various excipients in varying ratio and combinations. The excipients used in the trials are:
1. Stearic acid
2. Polyethylene oxide (PEO)
3. Kollidon® SR (Polyvinyl acetate and Povidone)
4. Calcium carbonate
5. Klucel™ JF (Hydroxypropyl cellulose)
6. Ethocel™ N7 (Ethyl cellulose)
7. Talc Screw Configuration:

The trials were performed using the twin screw extruder Omega 20 manufactured by the assignee herein with two different screw configurations F1 and F2, each with a Do/Di of 1.71. Both the F1 and F2 screw configurations are provided below in Table 1 and have been illustrated in FIGS. 5 and 6 respectively. FIGS. 5 and 6 illustrate a single shaft though the extruder configuration has a pair of shafts with complimentary elements. The F2 screw configuration differs from F1 in that the F2 has different neutral kneading block configuration which results in better fragmentation as compared to F1. Both configurations use a mixing element in the fragmenting zone. The mixing elements (DSE) as described in WO 2013/128463 are positioned at the beginning of the fragmenting zone (barrel C4). The cooling also begins with barrel C4.

TABLE 1

| Features | F1 Screw type Configuration | F2 Screw type Configuration |
| --- | --- | --- |
| Element length | 800 mm | 800 mm |
| Max. Screw Speed | 1200 rpm | 1200 rpm |

TABLE 1-continued

| Diameter | 19.6 mm | 19.6 mm |
|---|---|---|
| Percentage of kneading blocks | 21.82 | 19.95 |

Screw Elements

| Element Number | F1-Screw Element type | F2-Screw Element type |
|---|---|---|
| 1 | RSE 15/15-1 CHS | RSE 15/15-1 CHS |
| 2 | RFV 45/45 | RFV 45/45 |
| 3 | RFV 45/45 | RFV 45/45 |
| 4 | RFV 45/45 | RFV 45/45 |
| 5 | RFN 45/22.5 | RFN 45/22.5 |
| 6 | RSE 30/30 | RSE 30/30 |
| 7 | RSE 20/20 | RSE 20/20 |
| 8 | RSE 20/20 | RSE 20/20 |
| 9 | RSE 20/20 | RSE 20/20 |
| 10 | RSE 20/20 | RSE 20/20 |
| 11 | RKB 45/5/20 | RKB 45/5/20 |
| 12 | RKB 45/5/20 | RKB 45/5/20 |
| 13 | LSE 20/10 | LSE 20/10 |
| 14 | RSE20/20 | RSE20/20 |
| 15 | RSE 20/20 | RSE 20/20 |
| 16 | DSE 20/40 A2-A | DSE 20/40 |
| 17 | DSE 20/40 A2-A | DSE 20/40 |
| 18 | DSE 20/40 A2-A | DSE 20/40 |
| 19 | RKB 45/5/15 | RKB 45/5/15 |
| 20 | RSE 20/20 | RSE 20/20 |
| 21 | RKB 45/5/15 | RKB 45/5/15 |
| 22 | RSE 20/20 | RSE 20/20 |
| 23 | RKB 45/5/15 | NKB 90/5/15 |
| 24 | RSE 20/20 | RSE 20/20 |
| 25 | RKB 45/5/15 | NKB 90/5/15 |
| 26 | RSE 20/20 | RSE 20/20 |
| 27 | RKB 45/5/15 | NKB 90/5/15 |
| 28 | RSE 20/20 | RSE 20/20 |
| 29 | RKB 45/5/15 | NKB 90/5/15 |
| 30 | RSE 20/20 | RSE 20/20 |
| 31 | RKB 45/5/15 | NKB 90/5/15 |
| 32 | RSE 20/20 | RSE 20/20 |
| 33 | NKB 90/5/15 | NKB 90/5/15 |
| 34 | RSE 20/20 | RSE 30/15 |
| 35 | NKB 90/5/15 | RSE 20/20 |
| 36 | RSE 15/15 | RSE 15/15 |

List of Abbreviations for Elements
RSE—Right Handed Screw Element
RFV—Right Handed Shovel Element
RFN—Right Handed Transition Element
LSE—Left Handed Screw Element
DSE—Dynamic Stirring Element
RKB—45 degree stagger angle Right Handed Kneading Block
NKB—90 degree stagger angle (Neutral) Kneading Block Barrel Temperatures The melting point of Ketoprofen is known to be about 90° C. The temperature of the melting zone in the barrel is maintained at 60° C. in trial 13 (i.e. below the melting point of API). Cefuroxime axetil is an amorphous drug with a Tg of above 70° C.

Table 2 illustrates the various trials performed using the two drugs along with different excipients to obtain pharmaceutical composition in accordance with the present invention as well the trials conducted using excipients only. The API and/or the excipient (s), in the ratio provided in the table are blended and fed to the extruder. The barrel temperatures, screw configuration employed in each of the trials are also indicated in Table 2.

TABLE 2

| Trial No. | API and/or Excipient(s) | Screw configuration | Barrel temperatures | Particle size distribution (μ) | Surface Weighted Mean (SWM) (μ) | Volume Weighted Mean (VWM) (μ) |
|---|---|---|---|---|---|---|
| 1 | Stearic acid + Cefuroxime axetil (1:1) | F1 | RT, 60, 60, 60, 10, 10, 10, 10, 10 | d10-127 d50-617 d90-1322 | 222 | 679 |
| 2 | Stearic acid + Cefuroxime axetil (1:3.4) | F1 | RT, 60, 60, 60, 10, 10, 10, 10, 10 | d10-109 d50-550 d90-1216 | 229 | 617 |
| 3 | Stearic acid + Cefuroxime axetil (1:3.4) + 5% PEO | F1 | RT, 60, 60, 60, 10, 10, 10, 10, 10 | d10-86 d50-446 d90-1070 | 193 | 525 |
| 4 | Stearic acid + Cefuroxime axetil (1:3.4) + 10% PEO | F1 | RT, 60, 60, 60, 10, 10, 10, 10, 10 | d10-94 d50-474 d90-1161 | 210 | 561 |
| 5 | Kollidon SR | F1 | RT, 80, 80, 80, 10, 10, 10, 10, 10 | Mean particle diameter- larger than 1 mm | | |
| 6 | Kollidon SR + Stearic acid (1:1) | F1 | RT, 60, 60, 60, 10, 10, 10, 10, 10 | d10-524 d50-985 d90-1569 | 772 | 1013 |
| 7 | Kollidon SR (70%) + 30% Calcium carbonate | F1 | RT, 80, 80, 80, 10, 10, 10, 10, 10 | Mean particle diameter- larger than 1 mm | | |
| 8 | Klucel JF | F1 | RT, 140, 140, 140, 10, 10, 10, 10, 10 | Mean particle diameter- larger than 1 mm | | |
| 9 | Klucel JF + Stearic acid (1:1) | F1 | RT, 80, 80, 80, 10, 10, 10, 10, 10 | Mean particle diameter- larger than 1 mm | | |
| 10 | Klucel JF + Stearic acid (1:1) + 5% talc | F1 | RT, 80, 80, 80, 10, 10, 10, 10, 10 | Mean particle diameter- larger than 1 mm | | |
| 11 | Ethocel N7 + stearic acid (1:1) | F1 | RT, 80, 80, 80, 10, 10, 10, 10, 10 | Mean particle diameter- larger than 1 mm | | |

TABLE 2-continued

| Trial No. | API and/or Excipient(s) | Screw configuration | Barrel temperatures | Particle size distribution (μ) | Surface Weighted Mean (SWM) (μ) | Volume Weighted Mean (VWM) (μ) |
|---|---|---|---|---|---|---|
| 12 | Stearic acid + Cefuroxime axetil (1:3.4) | F2 | RT, 60, 60, 60, 10, 10, 10, 10, 10 | d10-40 d50-322 d90-781 | 98 | 379 |
| 13 | Stearic acid + Ketoprofen (1:3.4) | F2 | RT, 60, 60, 60, 10, 10, 10, 10, 10 | d10-81 d50-448 d90-1175 | 179 | 549 |
| 14 | Stearic acid | F2 | RT, 60, 60, 60, 10, 10, 10, 10, 10 | d10-47 d50-316 d90-773 | 115 | 374 |
| 15 | Kollidon SR | F2 | RT, 60, 60, 60, 10, 10, 10, 10, 10 | | Mean particle diameter-larger than 1 mm | |
| 16 | Kollidon SR + Stearic acid (1:1) | F2 | RT, 60, 60, 60, 10, 10, 10, 10, 10 | d10-273 d50-809 d90-1456 | 471 | 844 |
| 17 | Klucel JF + Stearic acid (1:1) | F2 | RT, 80, 80, 80, 10, 10, 10, 10, 10 | d10-401 d50-848 d90-1474 | 649 | 895 |
| 18 | Ethocel N7 + stearic acid (1:1) | F2 | RT, 80, 80, 80, 10, 10, 10, 10, 10 | d10-507 d50-959 d90-1550 | 776 | 993 |

(RT = Room Temperature)
For trials 5, 7, 8, 9, 10, 11 and 15 the mean particle diameter was larger than 1 mm.

Particle Size Distribution:

The particle size distribution of each of the composition prepared in accordance with trials listed in Table 2 was determined using a Malvern MasterSizer 2000. The mean particle diameter of the fragments obtained in each of the trial has also been listed in Table 2.

FIG. 8 shows the particle size analysis report for pharmaceutical composition prepared according to trial 12. As illustrated in the figure, the D(0.1), D(0.5), and D(0.9) values for the pharmaceutical composition are 40, 322 and 781 microns respectively. The surface weighted mean and volume weighted mean of the fragments was found to be 98 and 379 microns respectively.

As illustrated in table 2, comparable mean particle diameter is obtained in trials 1-4. Comparing trials 1 and 2, the effect of different drug loading on particle size distribution is observed. Comparing trials 2 and 12, the effect of screw configuration on particle size distribution is observed. Comparing trials 12 and 13, the effect of different drugs on particle size distribution is observed.

Trials Using Excipients Only:

Trials 5, 6, 7, 8, 9, 10, 11, 14, 15, 16, 17, 18 were conducted using excipients only, alone and in combination with other excipients.

Comparing trials 14 and 15, the effect of different excipients on particle size distribution is observed. Stearic acid being crystalline is more brittle than Kollidon SR that is amorphous and accordingly smaller particle size was obtained with stearic acid. The result of trial 14 also indicate that stearic acid, a difficult to mill excipient using conventional techniques, can also be used for pharmaceutical compositions using the hot melt fragmentation process described herein. Trials 16 through 18 illustrate the effect of a combination of excipients on the particle size distribution. Trials 16 through 18 also indicate that difficult to mill excipients can also be used for hot melt fragmentation in combination with other excipients. Similar results were observed in trials 5 and 6 using a different screw configuration.

Comparing trials 6 and 16, the effect of different screw configurations on the particle size distribution is observed. Fragments obtained using the screw configuration F2 were finer than using the screw configuration F1. Similar results were observed in trials 2 and 12; trials 11 and 18; and trials 9 and 17. It is believed that this is a direct result of the better fragmentation properties exhibited by F2 type screw configuration.

The above data suggests that altering the excipients, process parameters such as temperatures, screw configuration can be used to prepare fragments of desired size ranges.

Specific Embodiments are Described Below

A co-rotating twin screw extruder for forming fragments comprising an intake zone for receiving one or more excipient(s) suitable for oral dosage or one or more excipient(s) suitable for oral dosage along with one or more active pharmaceutical ingredient, a melt zone for softening at least one excipient to form a viscous mass or melt and a fragmenting zone for simultaneously fragmenting and cooling the viscous mass into cooled fragments and an extruder outlet for recovering the cooled fragments from the extruder.

Such extruder(s), wherein the fragmenting zone comprises of milling, mixing or fragmenting elements.

Such extruder(s), wherein the fragmenting zone comprises of at least one mixing element having a continuous flight helically formed thereon with a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead and transforms back to a non-integer lobe flight in a fraction of the lead 'L'.

Such extruder(s), wherein the fragmenting zone comprises of at least one mixing element and the mixing element is positioned at the beginning of the fragmenting zone.

Such extruder(s), wherein the excipient(s) is selected from the group consisting of a fatty acid, glyceryl behenate and waxes.

Such extruder(s), wherein the fatty acid is stearic acid.

Such extruder(s), wherein the temperature of the melt zone is above the softening temperature or glass transition temperature Tg or melting point of at least one excipient to enable formation of the viscous mass or melt.

Such extruder(s), wherein the fragmenting zone is provided with a cooling system and the temperature of the fragmenting zone is at or below the softening temperature or glass transition temperature Tg or melting point of at least one excipient for cooling the viscous mass or melt.

Such extruder(s), wherein the cooling is uniform throughout the fragmenting zone.

Such extruder(s), wherein the fragmenting zone has an increasing cooling gradient towards the extruder outlet.

Further Specific Embodiments are Described Below

A method of forming fragments within a co-rotating twin screw extruder comprising:
a. feeding one or more excipient(s) suitable for oral dosage into the extruder;
b. softening or melting at least one excipient to form a viscous mass or melt; and
c. simultaneously fragmenting and cooling the viscous mass or melt to obtain cooled fragments;
d. collecting the cooled fragments from the extruder.

Such method(s), comprising feeding one or more excipient(s) suitable for oral dosage along with one or more active pharmaceutical ingredient into the extruder.

Such method(s), wherein the excipient(s) is selected from the group consisting of a fatty acid, glyceryl behenate and waxes.

Such method(s), wherein the fatty acid is stearic acid.

Such method(s), wherein the simultaneous fragmenting and cooling is achieved by milling, mixing or fragmenting elements.

Such method(s), wherein the simultaneous fragmenting and cooling is achieved by at least one mixing element having a continuous flight helically formed thereon with a lead 'L', wherein either the flight transforms at least once from an integer lobe flight into a non-integer lobe flight in a fraction of the lead 'L' and transforms back to an integer lobe flight in a fraction of the lead or the flight transforms at least once from a non-integer lobe flight into an integer lobe flight in a fraction of the lead 'L' and transforms back to a non-integer lobe flight in a fraction of the lead 'L'.

Such method(s), wherein the mixing element is positioned at the beginning of the fragmenting zone.

INDUSTRIAL APPLICABILITY

The disclosed process for the manufacture of pharmaceutical compositions using an extruder finds application in size controlled manufacturing of various drug dosage forms. Fragments may be obtained for tablet compression, capsule filling and for preparing sprinkles or suspensions for oral administration without involving complex downstream auxiliary equipments. The pharmaceutical composition obtained using the disclosed process may result in improved characteristics such as enhancement of the dissolution rate and/or bio-availability of the drug, controlled release of the drug, taste masking, stability enhancement etc. The present process also prevents contamination and reduces any yield loss of the pharmaceutical composition, encountered in multi-equipment processes viz. conventional Granulation/compaction processes or conventional Hot Melt Extrusion process.

The disclosed process is suitable for all excipients, especially difficult to mill excipients such as stearic acid. The simultaneous cooling and fragmenting using fragmenting or mixing elements in the fragmentation zone aids in obtaining the desired fragments.

The extruder as disclosed is suitable for forming pharmaceutical fragments using all excipients, particularly difficult to mill excipients such as stearic acid.

We claim:

1. A co-rotating twin screw extruder for forming fragments comprising an intake zone for receiving one or more excipient(s) suitable for oral dosage or one or more excipient(s) suitable for oral dosage along with one or more active pharmaceutical ingredient(s), a melt zone for softening at least one excipient to form a viscous mass or melt, a fragmenting zone and an extruder outlet, the fragmenting zone comprising at least one element having a continuous flight helically formed thereon with a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L', for simultaneous fragmenting and cooling the viscous mass into cooled fragments, and wherein the cooled fragments are recovered from the extruder outlet of the extruder.

2. A co-rotating twin screw extruder as claimed in claim 1, wherein the fragmenting zone comprises of milling, mixing or fragmenting elements.

3. A co-rotating twin screw extruder as claimed in claim 1, wherein the mixing element is positioned at a beginning of the fragmenting zone.

4. A co-rotating twin screw extruder as claimed in claim 1, wherein the excipient(s) is selected from the group consisting of a fatty acid, glyceryl behenate and waxes.

5. A co-rotating twin screw extruder as claimed in claim 4, wherein the fatty acid is stearic acid.

6. A co-rotating twin screw extruder as claimed in claim 1 wherein the temperature of the melt zone is above the softening temperature or glass transition temperature Tg or melting point of at least one excipient to enable formation of the viscous mass or melt.

7. A co-rotating twin screw extruder as claimed in claim 1 wherein the fragmenting zone is provided with a cooling system and the temperature of the fragmenting zone is at or below the softening temperature or glass transition temperature Tg or melting point of at least one excipient for cooling the viscous mass or melt.

8. A co-rotating twin screw extruder as claimed in claim 1 wherein the cooling is uniform throughout the fragmenting zone.

9. A co-rotating twin screw extruder as claimed in claim 1 wherein the fragmenting zone has an increasing cooling gradient towards the extruder outlet.

10. A method of forming fragments within a co-rotating twin screw extruder comprising:
a. feeding one or more excipient(s) suitable for oral dosage into the extruder;
b. softening or melting at least one excipient to form a viscous mass or melt;
c. simultaneously fragmenting and cooling the viscous mass or melt by using, at least one mixing element having a continuous flight helically formed thereon with a lead 'L', wherein either the flight transforms at least once from an integer lobe flight into a non-integer lobe flight in a fraction of the lead 'L' and transforms back to an integer lobe flight in a fraction of the lead 'L' or the flight transforms at least once from a non-integer lobe flight into an integer lobe flight in a fraction of the lead 'L' and transforms back to a non-integer lobe flight in a fraction of the lead 'L' in the fragmenting zone to obtain cooled fragments within the extruder; and d. collecting the cooled fragments from the extruder.

11. A method as claimed in claim 10 comprising feeding one or more excipient(s) suitable for oral dosage along with one or more active pharmaceutical ingredient into the extruder.

12. A method as claimed in claim 10 wherein the excipient(s) is selected from the group consisting of a fatty acid, glyceryl behenate and waxes.

13. A method as claimed in claim 12 wherein the fatty acid is stearic acid.

14. A method as claimed in claim 10 wherein the simultaneous fragmenting and cooling is achieved by milling, mixing or fragmenting elements.

15. A method as claimed in claim 10 wherein the mixing element is positioned at the beginning of the fragmenting zone.

* * * * *